(12) United States Patent
Lisec

(10) Patent No.: US 8,535,933 B2
(45) Date of Patent: Sep. 17, 2013

(54) METHOD AND PROCESS FOR CLEANING PIPES AND COMPONENTS IN A PIPED MEDICAL VACUUM SYSTEM

(76) Inventor: Scott E. Lisec, Clayton, NC (US)

( * ) Notice: Subject to any disclaimer, the term of this patent is extended or adjusted under 35 U.S.C. 154(b) by 0 days.

(21) Appl. No.: 13/344,452

(22) Filed: Jan. 5, 2012

(65) Prior Publication Data

US 2013/0011910 A1    Jan. 10, 2013

Related U.S. Application Data

(60) Provisional application No. 61/430,001, filed on Jan. 5, 2011.

(51) Int. Cl.
    *C12Q 1/00*      (2006.01)

(52) U.S. Cl.
    USPC ........................................................ 435/264

(58) Field of Classification Search
    None
    See application file for complete search history.

(56) References Cited

U.S. PATENT DOCUMENTS

5,697,918 A * 12/1997 Fischer et al. ................. 604/227
5,908,297 A * 6/1999 Fill et al. ........................ 433/95

OTHER PUBLICATIONS

"Dental Vacuum Line Cleaners: A Pollution Prevention Perspective" (2005), Dental P2 Project, 1-7.*
Keith, Vital Design: How Engineers can help doctors save lives with properly functioning medical gas and vacuum systems, (2010), Plumbing Systems & Design, 18-23.*

* cited by examiner

*Primary Examiner* — Ralph Gitomer
*Assistant Examiner* — Teresa E Knight
(74) *Attorney, Agent, or Firm* — Joseph S. Heino; Patrick M. Bergin

(57) ABSTRACT

A method and process is provided to help increase flow within the piping of a clinical vacuum system under low flow inlet conditions and to re-establish flow under zero flow inlet conditions, among other things. The method and process broadly uses the steps of isolating and accessing the piping of the clinical vacuum system, introducing an enzymatic solution to the piping, and then extracting the solution following exposure of the solution to the piping to remove complex organic materials from the piping. A portable collection canister can be used to measure the amount of enzymatic solution that is put into the piping and removed from the piping to ensure that the system is dry. The collection canister can be connected via hose to a zone valve box of the system or to a service valve of the system.

15 Claims, 1 Drawing Sheet

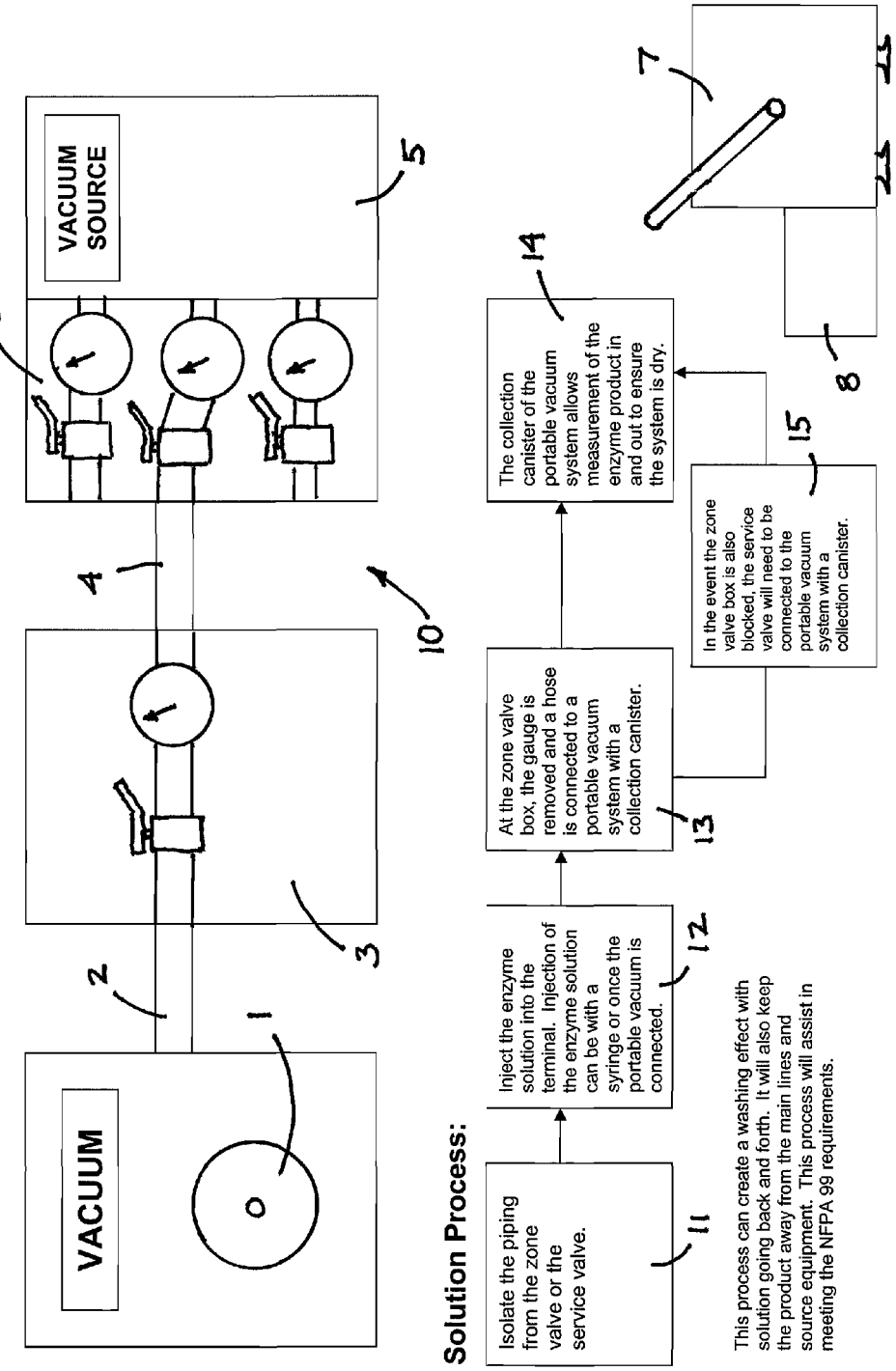

METHOD AND PROCESS FOR CLEANING PIPES AND COMPONENTS IN A PIPED MEDICAL VACUUM SYSTEM

This application claims the benefit of U.S. Provisional Application No. 61/430,001, filed Jan. 5, 2011.

FIELD OF THE INVENTION

This invention relates generally to piped medical gas systems, including piped medical vacuum systems, of the clinical type that are installed and used in medical facilities. More specifically, it relates to a method and process for cleaning the pipes and other components that are used in such a piped medical vacuum system for the purpose of removing fluid and tissue debris from vacuum system pipes and maintaining or re-establishing the efficiency of performance of the vacuum system.

BACKGROUND OF THE INVENTION

Medical facilities are typically provided with a centrally piped system for accessing medical gases and for providing clinical vacuum suction. Clinical suction, or aspiration, represents an absolutely necessary tool in all surgical procedures and must be readily available and fully functional in all surgical and procedure suites, as well as in post-surgery recovery areas. Clinical suction is necessary to clear fluids and tissue debris from patients during such surgical procedures and to facilitate physical and visual access to the field of view during the performance of the clinical procedure. The efficiency of a clinical vacuum suction system can be compromised where lint, debris or dried body fluids accumulate over time and work to reduce vacuum system performance. When aspiration becomes slow and difficult, it is imperative that the vacuum system be cleaned. Reduced efficiencies can also result in the failure of the clinical vacuum suction system to comply with certain mandatory regulatory requirements. For example, the National Fire Protection Association's NFPA 99, "Health Care Facilities," regulations cover, among other things, the installation and maintenance of such clinical vacuum systems, requiring that systems maintain a minimum extraction rate in standard cubic feet per minute.

In the view of this inventor, there is a clear need to establish routine preventative maintenance of clinical vacuum suction systems to avoid the accumulation of debris within the system, to prevent suction problems and to ensure the continued good performance of the entire vacuum system, including the vacuum piping system and to the secondary equipment that may be attached to it. In the experience of this inventor, there is a solution to this need, and the solution relates to the introduction of an enzymatic solution into the vacuum piping system in accordance with the present invention.

SUMMARY OF THE INVENTION

In accordance with the foregoing, this inventor has devised a method and process to help increase flow within the piping of a clinical vacuum system under low flow inlet conditions and to re-establish flow under zero flow inlet conditions, among other things. The method and process broadly uses the steps of isolating and accessing the piping of the clinical vacuum system, introducing an enzymatic solution to the piping, and then extracting the solution following exposure of the solution to the piping.

The foregoing and other features of the method and process of the present invention will become apparent from the detailed description that follows.

BRIEF DESCRIPTION OF THE DRAWINGS

FIG. 1 is a schematic diagram illustrating the method and process of the present invention.

DETAILED DESCRIPTION

Referring now to FIG. 1, it illustrates the essential steps of the method and process of the present invention. It is assumed for purposes of this disclosure that the clinical vacuum system, generally identified 10, with which the method and process can be used comprises several essential components. One component is the vacuum terminal 1, which is that portion of the system 10 at which the user can access the system 10 from within the surgical suite or the medical procedure room. Another component is the piping 2, 4 leading from the vacuum terminal 1 to a vacuum source 5, which is typically a vacuum pump. At some point between the vacuum terminal 1 and pump 5 is a service valve 6, which controls access to the vacuum source 5, and a zone valve box 3, which provides gauging for measuring the vacuum extraction rate that is available in the piping 2, 4 during normal operation and provides a secondary control for access to the vacuum source 5. That is, both the service valve 6 and the zone valve 3 are capable of providing (by opening) or preventing (by shutting off) access to the vacuum source 5.

In the method and process of the present invention, there may be an indication that the vacuum terminal is restricted or blocked. However, such is not necessary for initiation of implementation of the method and process of the present invention where, for example, use of the method and process is purely for preventative maintenance purposes. Accordingly, the presence of a flow restriction or blockage is not a limitation of the present invention.

In the event of a restricted or low flow condition, the piping 2, 4 from the zone valve 3 or the service valve 6 must first be isolated 11, which means that the subject piping 2, 4 is not then subjected to a vacuum condition. The subject piping 2, 4 is simply brought to atmospheric pressure.

An enzymatic solution is then provided 12. In the preferred embodiment, the solution is a combination of enzymes that penetrate and accelerate the break-down of complex organic materials such as blood, proteins, fats and oils, transforming them into simpler compounds which can then break into fragments. When these substances break into fragments, they are more easily removed from the vacuum system 10. In the preferred embodiment, it is desirable to provide a solution that naturally deactivates within forty-eight hours after use. It is also desirable to provide a solution that is safe for all vacuum pipeline materials and components.

Once the piping is isolated 11, the enzymatic solution is injected 12 into the vacuum terminal 1. Injection 12 can be accomplished by use of a syringe (not shown). The use 14 of a portable vacuum system 7 with a collection canister 8 is also preferred so as to keep the solution away from the vacuum source 5 equipment, such as the vacuum pump. The use of the collection canister 8 of the portable vacuum system 7 allows measurement of the solution in and out to ensure that the isolated system is dry upon completion of the procedure.

One end of a tubing (also not shown) is attached to the syringe tip and the other end is attached to a vacuum adapter. The vacuum adapter is plugged into the vacuum inlet 1 and} the solution 12 is injected into the vacuum terminal 1. The adapter is then removed immediately after the solution has been introduced.

At the zone valve box 3, the gauge is removed, and a hose from the portable vacuum system 7 is connected 13, 14 at that point in the piping. In the event that the zone valve box is also blocked, the service valve 6 will need to be connected 14, 15 to the hose of the portable vacuum system 7. The collection canister 8 of the portable vacuum system 7 allows measurement of the enzyme product that is introduced into and extracted out of the vacuum piping 2, 4 and components to ensure that the system piping is dry upon completion of the procedure.

The enzymatic solution may be left in the vacuum terminal 1 for an extended period of time, preferably about thirty minutes. To remove the solution from the vacuum terminal, the syringe set up with the vacuum adapter is plugged into the vacuum inlet and the solution is slowly extracted out of the terminal. The solution should then be disposed of and treated as contaminated waste.

In an alternative embodiment, the method and process of the present invention can also be used in a "washing" effect, with solution flowing back and forth along the piping.

Where there is a zero flow inlet condition, the vacuum terminal 1 should be disassembled. A disposable container is used to hold a measured quantity of the enzymatic solution. The vacuum terminal components are then added to the container and allowed to soak. Any excess debris is then removed from the components and the vacuum terminal is re-assembled. The solution should be disposed of and treated as contaminated waste. The inlet is then tested to ensure acceptable flow prior to placing it back in service.

After the vacuum piping and components are cleaned and all solution is removed, the zone valve or isolation valve should be returned to the operable (open/on) position and the vacuum inlet should be allowed to flow freely for a period of time, preferably one to five minutes. Again, the inlet should be tested to ensure acceptable flow prior to placing it back in service.

The details of the invention having been disclosed in accordance with the foregoing, I claim:

1. A method for cleaning a piped medical vacuum system, the vacuum system comprising a vacuum source, piping and complex organic materials contained within the piping, the method comprising the steps of:
   isolating the piping of the centrally piped vacuum system provides clinical vacuum suction to a surgical suite or medical procedure suite;
   accessing the piping of the vacuum system;
   introducing an enzymatic solution to the piping of the vacuum system;
   exposing the enzymatic solution to the piping and to the complex organic materials contained in the piping;
   providing a collection canister to keep solution away from the vacuum source; and
   extracting the solution and the complex organic materials from the piping of the vacuum system into the collection canister.

2. The cleaning method of claim 1 wherein isolating the piping comprises the subject piping is not subjected to a vacuum condition but is brought to atmospheric pressure.

3. The cleaning method of claim 1 wherein introducing the enzymatic solution comprises injecting the solution is injected into the piping with a syringe.

4. The cleaning method of claim 1 wherein introducing the enzymatic solution comprises providing a solution that is a combination of enzymes that penetrate and accelerate the break-down of complex organic materials, including, blood, protein, fats and oils, thereby transforming them into simpler compounds which can then break into fragments which are more easily removed from the vacuum system.

5. The cleaning method of claim 4 wherein the solution provided naturally deactivates within a given time following its introduction into the system and is safe all vacuum pipeline materials and components.

6. The cleaning method of claim 1 wherein the use of the collection canister allows measurement of the solution into and out of the system.

7. The cleaning method of claim 6 wherein the vacuum system further comprises a zone valve box and the method further comprises the step of connecting the collection canister to the zone valve box.

8. The cleaning method of claim 6 wherein the vacuum system further comprises a service valve and the method further comprises the step of connecting the collection canister to the service valve.

9. A process for cleaning a piped medical vacuum system, the vacuum system comprising a vacuum terminal for accessing the system from within a surgical suite or a medical procedure room; a vacuum source; piping leading from the terminal to the vacuum source; a service valve disposed at a point between the terminal and the source; a zone valve box disposed at a point between the terminal and the source; and complex organic materials contained within the piping; the process comprising the steps of:
   isolating the piping of the vacuum system from the vacuum terminal to the zone valve or the service valve;
   accessing the piping of the vacuum system between the vacuum terminal and the zone valve or the service valve;
   introducing an enzymatic solution to the piping at the vacuum terminal of the vacuum system;
   exposing the enzymatic solution to the piping and to the complex organic materials contained in the piping between the vacuum terminal and the zone valve or the service valve;
   providing a collection canister to keep solution away from the vacuum source; and
   extracting the solution and the complex organic materials from the piping of the vacuum system into the collection canister.

10. The cleaning process of claim 9 wherein isolating the piping comprises the subject piping is not subjected to a vacuum condition but is brought to atmospheric pressure.

11. The cleaning process of claim 9 wherein introducing the enzymatic solution comprises injecting the solution is injected into the piping with a syringe.

12. The cleaning process of claim 9 wherein introducing the enzymatic solution comprising providing a solution that is a combination of enzymes that penetrate and accelerate the break-down of complex organic materials, including, blood, protein, fats and oils, thereby transforming them into simpler compounds which can then break into fragments which are more easily removed from the vacuum system.

13. The cleaning process of claim 12 wherein the solution provided naturally deactivates within a given time following its introduction into the system and is safe all vacuum pipeline materials and components.

14. The cleaning process of claim 9 wherein the use of the collection canister allows measurement of the solution into and out of the system.

15. The cleaning process of claim 9 wherein the vacuum source is a vacuum pump.

* * * * *